(12) United States Patent
Small

(10) Patent No.: US 7,736,002 B2
(45) Date of Patent: Jun. 15, 2010

(54) SUSPENDED SLIT LAMP

(76) Inventor: Kent W. Small, 3134 Corda Dr., Los Angeles, CA (US) 90049

( * ) Notice: Subject to any disclaimer, the term of this patent is extended or adjusted under 35 U.S.C. 154(b) by 0 days.

(21) Appl. No.: 12/044,833

(22) Filed: Mar. 7, 2008

(65) Prior Publication Data

US 2009/0225279 A1 Sep. 10, 2009

(51) Int. Cl.
  *A61B 3/10* (2006.01)
(52) U.S. Cl. .................. 351/214; 351/221; 351/246
(58) Field of Classification Search .................. 351/214
  See application file for complete search history.

(56) References Cited

U.S. PATENT DOCUMENTS

| | | | |
|---|---|---|---|
| 3,944,342 A * | 3/1976 | Martinez | 351/206 |
| 4,102,565 A * | 7/1978 | Takizawa et al. | 351/214 |
| 4,796,859 A | 1/1989 | Ventura | |
| 5,230,347 A * | 7/1993 | Weinstein et al. | 600/553 |
| 5,420,716 A * | 5/1995 | Fukaya | 359/368 |
| 6,283,596 B1 | 9/2001 | Yoshimura et al. | |
| 6,364,268 B1 | 4/2002 | Metelski | |
| RE38,672 E | 12/2004 | Grinblat | |
| 6,981,946 B2 * | 1/2006 | Davidson | 600/405 |
| 7,052,135 B2 | 5/2006 | Takeda et al. | |
| 7,093,813 B1 | 8/2006 | Zirps et al. | |
| 7,219,472 B2 | 5/2007 | Gallant et al. | |
| 2005/0092874 A1 * | 5/2005 | Lawhorn et al. | 248/127 |

* cited by examiner

Primary Examiner—Jessica T Stultz
(74) Attorney, Agent, or Firm—Perkins Coie LLP

(57) ABSTRACT

A slit lamp apparatus is suspended from a support structure such that no examination table is required in front of a patient during an examination. Accordingly, a patient's interaction with the slit lamp apparatus is unobstructed. Individual components of the slit lamp apparatus are optionally movable such that they may be positioned in desired positions relative to a patient's eye during an examination.

20 Claims, 1 Drawing Sheet

SUSPENDED SLIT LAMP

BACKGROUND

Slit lamp systems are commonly used by ophthalmologic and optometric practitioners for performing general eye examinations. The body of a typical slit lamp system includes an illumination component and an observation component. The illumination component emits an adjustable slit-shaped beam of light, or slit light, and background illumination light for illuminating the eye to be examined. The observation component typically includes a biomicroscope for magnifying a portion or cross-sectional image of the eye illuminated by the slit light. Slit lamp systems may also include an imaging apparatus associated with the observation component, such as a camera or a video camera, either of which may optionally be associated with a computer, for converting images viewed through the observation component into tangible visual images to be stored or studied after completion of the examination.

In a common configuration, the illumination and observation components are supported on an examination table. The table is typically attached to a stand via an arm that is movable about the stand so that the table may be positioned front of a patient. The table typically supports a headrest, which may include a chin rest and a forehead rest for steadily holding a patient's head during an examination.

To conduct a typical examination, the practitioner maneuvers the examination table in front of the patient, such that the headrest is directly in front of the patient. The patient then leans forward so that his or her chin and forehead come to rest on or against the chin and forehead rests, respectively. This ensures that the patient's head remains relatively stationary during the examination. Thereafter, the practitioner illuminates the patient's eye with the illumination component and observes the eye via the observation component.

One limitation associated with currently available slit lamp systems is that the examination table supporting the slit lamp system often makes it difficult to appropriately position the patient, which may cause the patient discomfort. For example, when the patient leans forward to place his or her head on the headrest, the table may create a hindrance to the correct positioning of the patient's head. This may also prevent the practitioner from performing an adequate examination. These problems may occur when, for example, the patient has back pain, is obese, or has large breasts.

SUMMARY

A slit lamp apparatus is suspended from a support structure such that no examination table is required in front of a patient during an examination. Accordingly, a patient's interaction with the slit lamp apparatus is unobstructed. Individual components of the slit lamp apparatus are optionally movable such that they may be positioned in desired positions relative to a patient's eye during an examination.

Other features and advantages will appear hereinafter. The features described above can be used separately or together, or in various combinations of one or more of them.

DETAILED DESCRIPTION

Figure 1:
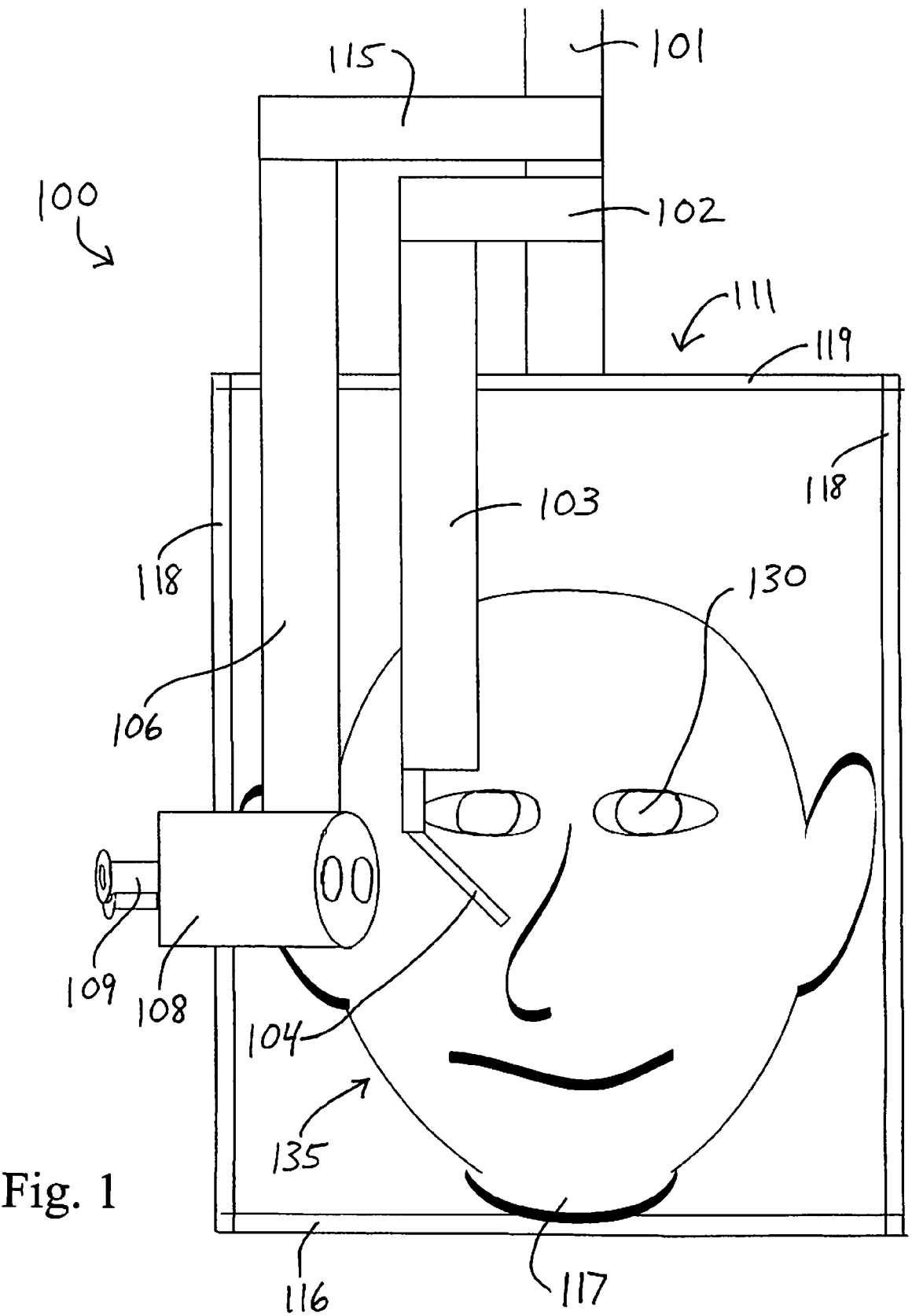
FIG. 1 is a perspective view of an inverted slit lamp apparatus, according to one embodiment.

Various embodiments of the invention will now be described. The following description provides specific details for a thorough understanding and enabling description of these embodiments. One skilled in the art will understand, however, that the invention may be practiced without many of these details. Additionally, some well-known structures or functions may not be shown or described in detail so as to avoid unnecessarily obscuring the relevant description of the carious embodiments.

The terminology used in the description provided below is intended to be interpreted in its broadest reasonable manner, even though it is being used in conjunction with a detailed description of certain specific embodiments of the invention. Certain terms may even be emphasized below. However, any terminology intended to be interpreted in any restricted manner will be overtly and specifically defined as such in this detailed description section.

Where the context permits, singular or plural terms may also include the plural or singular term, respectively. Moreover unless the word "or" is expressly limited to mean only a single item exclusive from the other items in a list of two or more items, then the use of "or" in such a list is to be interpreted as including (a) any single item in the list, (c) all of the items in the list, or (c) any combination of items in the list.

Turning now in detail to the drawing, FIG. 1 illustrates one embodiment of an inverted slit lamp apparatus 100 mounted on a support structure, such as a support arm 101. The support arm 101 may be connected to a stand, a ceiling (or ceiling module), a wall (or wall module), or any other suitable mechanism or mount. For ease of description, only a support arm 101 connected to a stand, which may optionally rest on a floor or other suitable location, will be described herein.

A headrest 111 and other components of the slit lamp apparatus 100 are preferably directly or indirectly attached to the support arm 101. In one embodiment, a top arm 119 of the headrest 111 is connected to the support arm 101, optionally in a pivotal manner. The headrest 111 includes side arms 118 extending downwardly from the top arm 119. A chin rest bar 116 for supporting the chin 117 of the patient 135 is preferably attached to or integral with the bottom ends of the two side arms 118.

A forehead rest bar (not shown) may optionally be attached to approximate mid-regions of the support arms 118 for supporting the forehead of the patient 135. The forehead rest bar, if included, may optionally be vertically adjustable along the side arms 118 so that a space between the chin rest bar and the forehead rest bar may be adjusted to correspond to the distance between the forehead and chin of a given patient. Any suitable head supporting features may additionally or alternatively be provided. In one embodiment, the chin rest bar 116 or the forehead rest bar may be omitted.

A first examination arm 103, which supports an illumination component 104 of the slit lamp apparatus 100, is preferably pivotally attached to the support arm 101 via a first hinge element or pivot element 102. The illumination component 104 is preferably a high-intensity light source that can be focused to shine a slit of light toward an eye 130 of a patient 135.

A second examination arm 106, which supports an observation component 108 of the slit lamp apparatus 100, is preferably pivotally attached to the support arm 101 via a second hinge element or pivot element 115. The observation component 108 preferably includes a microscope, such as a biomicroscope, including an eyepiece 109 for visual inspection of the patient's eye 130. In an alternative embodiment, the illumination and observation components 104, 108 may each be supported at different vertical locations on the same examination arm.

Any or all of the support arm 101, the first examination arm 103, and the second examination arms 103, 106 may optionally be vertically extendible via a telescoping arrangement or other suitable adjustment mechanism. This allows the slit lamp apparatus 100, or the individual illumination and observation components 104, 108, to be readily adjusted into desired vertical positions relative to a patient's eye 130.

An imaging apparatus, such as a camera or a video camera, either of which may be associated with a computer, may optionally be electrically connected or otherwise associated with the observation component 108. Such an imaging apparatus may be used to convert images viewed through the observation component 108 into tangible visual images that may be studied after completion of the examination.

In one embodiment, the support arm 101 may be attached to an axis-movement system (not shown), such as a track system, for providing longitudinal and or lateral (i.e., forward and backward or side-to-side) movement of the slit lamp apparatus 100. In another embodiment, the support arm 101 may be attached to rotation-based movement system (not shown), such as a rotating support plate, for providing rotational movement to the slit lamp apparatus 100. Any movement system employed may be a manually operable, friction-based system, a motorized system, or any other suitable movement system.

To perform an eye examination using the inverted slit lamp apparatus 100, in one embodiment, a practitioner vertically adjusts the forehead rest bar (if provided) such that it is spaced from the chin rest bar 116 a distance corresponding to a distance between a patient's chin 117 and forehead. The practitioner then moves the headrest 111 toward the patient 135, or the patient 135 moves his or her head toward the headrest 111, so that the patient's forehead and chin come to rest against or on the forehead rest bar and the chin rest bar 116, respectively. Alternatively, the practitioner may initially position the chin rest bar 116 under the patient's chin 117, and may then vertically adjust the forehead rest bar. Because the slit lamp apparatus 100 is suspended from above the patient, the patient may be seated in a comfortable posture, with no intrusion from an examination table or other potentially intrusive structure, while resting his or her head on the headrest 111.

The practitioner may then move or rotate, as necessary, the illumination and observation components 104, 108 into appropriate examination positions relative to the patient's eye 130. Next, the practitioner illuminates the patient's eye 130 with a slit of light generated by the illumination component 104, while observing the eye 130 through the eyepiece 109 on the observation component 108. If included, an imaging apparatus associated with the observation component 108 may provide one or more tangible images of the patient's eye 130 for the practitioner to further examine on a computer or similar device. When the examination is completed, the practitioner may move the slit lamp apparatus 100 away from the patient, or the patient may move back away from the slit lamp apparatus 100.

Any of the above-described embodiments may be used alone or in combination with one another. Furthermore, the slit lamp apparatus may include additional features not described herein. While several embodiments have been shown and described, various changes and substitutions may of course be made, without departing from the spirit and scope of the invention. The invention, therefore, should not be limited, except by the following claims and their equivalents.

What is claimed is:

1. An inverted slit lamp apparatus, comprising:
    a support structure;
    a headrest suspended downwardly from the support structure;
    a first arm suspended downwardly from the support structure;
    an illumination component, including a slit lamp, attached to the first arm;
    a second arm suspended downwardly from the support structure; and
    an observation component, including a microscope, attached to the second arm.

2. The apparatus of claim 1 wherein at least one of the first arm and the second arm is pivotally attached to the support structure.

3. The apparatus of claim 1 wherein at least one of the first arm and the second arm is vertically adjustable.

4. The apparatus of claim 1 wherein the headrest includes at least one of a chin rest bar and a forehead rest bar.

5. The apparatus of claim 1 wherein the support structure comprises a support arm projecting downwardly from a mechanism or mount.

6. The apparatus of claim 5 wherein the mechanism or mount comprises one of a stand, a ceiling, a ceiling module, a wall, and a wall module.

7. The apparatus of claim 5 wherein the support arm is vertically adjustable.

8. The apparatus of claim 1 wherein the support structure is attached to a movement system providing at least one of longitudinal, lateral, and rotational movement to the support structure.

9. The apparatus of claim 8 wherein the movement system comprises a manually operable, friction-based system.

10. The apparatus of claim 8 wherein the movement system is motorized.

11. A method for performing an eye examination, comprising:
    providing an inverted slit lamp apparatus suspended downwardly from a support structure, the inverted slit lamp apparatus including a headrest, an illumination component, and an observation component;
    positioning the headrest in front of a patient,
    moving the apparatus toward the patient, or the patient moving toward the apparatus, so the patient's head comes to rest against or on the headrest;
    moving the illumination component and the observation component into examination positions relative to an eye of the patient;
    focusing a slit of light from the illumination component onto the eye of the patient to illuminate the eye; and
    observing the illuminated eye via the observation component.

12. The method of claim 11 further comprising vertically adjusting a forehead rest on the headrest so that a space between a chin rest on the headrest and the forehead rest corresponds to a distance between a forehead and a chin of the patient.

13. The method of claim 11 wherein the positioning and moving steps are manually performed.

14. The method of claim 11 wherein at least one of the moving steps is motorized.

15. An inverted slit lamp apparatus, comprising:
a support arm connected to a support mechanism or mount;
a headrest suspended downwardly from the support arm;
a first examination arm suspended downwardly from, and pivotally attached to, the support arm;
an inverted illumination component, including a slit lamp, attached to the first examination arm;
a second examination arm suspended downwardly from, and pivotally attached to, the support arm; and
an inverted observation component, including a microscope, attached to the second examination arm.

16. The apparatus of claim 15 wherein at least one of the first examination arm and the second examination arm is vertically adjustable.

17. The apparatus of claim 15 wherein the support mechanism or mount comprises one of a stand, a ceiling, a ceiling module, a wall, and a wall module.

18. The apparatus of claim 15 wherein the support arm is attached to a movement system providing at least one of longitudinal, lateral, and rotational movement to the support arm.

19. An inverted slit lamp apparatus, comprising:
a support structure;
inverted illumination means for illuminating an eye, the inverted illumination means suspended downwardly from, and movable relative to, the support structure; and
inverted observation means for providing observation of the illuminated eye, the inverted observation means suspended downwardly from, and movable relative to, the support structure.

20. The slit lamp apparatus of claim 19 further comprising a headrest attached to, and projecting downwardly from, the support structure.

* * * * *